(12) United States Patent
Johansson

(10) Patent No.: US 6,929,618 B1
(45) Date of Patent: Aug. 16, 2005

(54) MICRODIALYSIS PROBE

(75) Inventor: Roger Johansson, Knivsta (SE)

(73) Assignee: CMA/Microdialysis AB, Solna (SE)

( * ) Notice: Subject to any disclaimer, the term of this patent is extended or adjusted under 35 U.S.C. 154(b) by 272 days.

(21) Appl. No.: 10/030,924

(22) PCT Filed: Jul. 14, 2000

(86) PCT No.: PCT/SE00/01495

§ 371 (c)(1),
(2), (4) Date: May 20, 2002

(87) PCT Pub. No.: WO01/03752

PCT Pub. Date: Jan. 18, 2001

(30) Foreign Application Priority Data

Jul. 14, 1999 (SE) .................... 9902695

(51) Int. Cl.[7] ........... A61M 37/00; B01D 61/00; C02F 1/44
(52) U.S. Cl. ........... 604/6.16; 604/4.01; 604/27; 210/645; 210/650
(58) Field of Search .......... 604/4.01, 5.01–5.04, 604/6.09, 6.1, 19, 27–29, 39, 43, 500, 506–8, 604/264, 268, 523, 529, 532–5; 128/898; 210/645–7, 210/650–2, 348, 321.6, 321.72, 321.61, 321.87

(56) References Cited

U.S. PATENT DOCUMENTS

| | | | |
|---|---|---|---|
| 4,989,608 A | | 2/1991 | Ratner |
| 5,106,365 A | * | 4/1992 | Hernandez .................. 604/27 |
| 5,441,481 A | | 8/1995 | Mishra et al. |
| 5,607,390 A | * | 3/1997 | Patsalos et al. ............. 604/29 |
| 5,735,832 A | | 4/1998 | Karlsson |
| 5,782,764 A | | 7/1998 | Werne |
| 5,817,017 A | | 10/1998 | Young et al. |
| 6,272,370 B1 | * | 8/2001 | Gillies et al. ............. 600/411 |
| 2003/0236454 A1 | * | 12/2003 | Liska et al. ............... 600/363 |

* cited by examiner

Primary Examiner—Patricia Bianco
(74) Attorney, Agent, or Firm—Young & Thompson

(57) ABSTRACT

A microdialysis probe includes a dialysis membrane located and supported between a closed distal end of the probe and a proximal end of the same, the membrane essentially surrounding a space for passage of perfusion liquid. The probe has an inlet and outlet for perfusion liquid, where a position indicating object at the distal part of the probe allows non-invasive examination of the location of the distal part of the microdialysis probe.

20 Claims, 3 Drawing Sheets

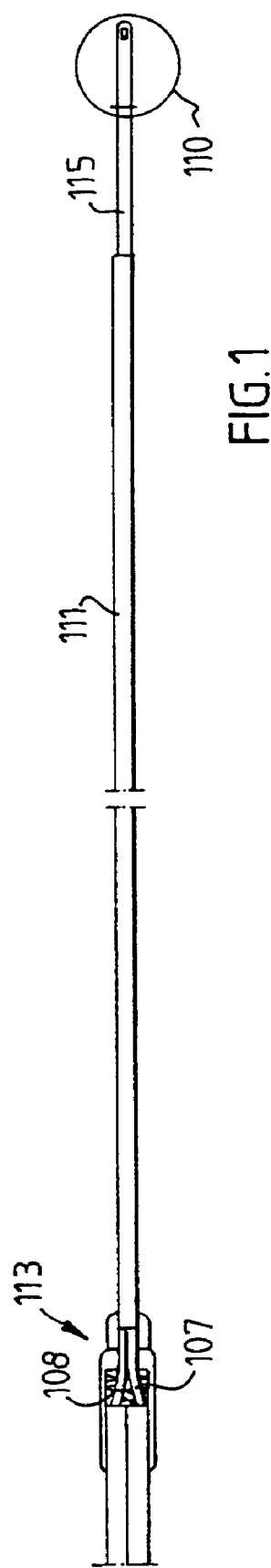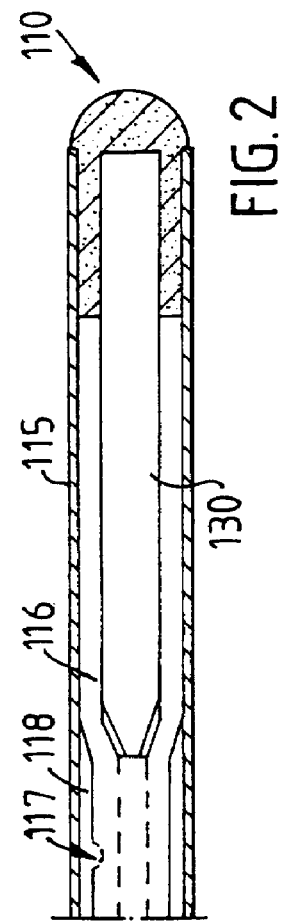

MICRODIALYSIS PROBE

FIELD OF THE INVENTION

The invention relates to a microdialysis probe. Microdialysis probes of this kind are described in SE-C-434 214, U.S. Pat. No. 5,735,832 and U.S. Pat. No. 5,741,284.

The meaning of specific wordings in this text should be interpreted as follows:

The word probe should be interpreted also as catheter.

The inlet and outlet of the probe as described may in case of a reversed flow be used as outlet and inlet, respectively.

Perfusion liquid is the liquid used in the microdialysis, which is allowed to enter the probe and there take up substances from the surrounding tissue through a membrane.

The perfusion liquid becomes the dialysate after the dialysis.

Non-Invasive investigating examination in this document refers to e.g. X-ray, NMR or the like techniques.

BACKGROUND OF THE INVENTION

Microdialysis is a method of examination in which a probe is inserted into tissue in vivo, such that one side of a semi-permeable membrane is in contact with tissue and extra cellular liquid and the other side is flushed or rinsed with a dialysis liquid (perfusate) which takes-up substances from the extra cellular liquid through the membrane. These substances can then be analyzed in the dialysate on or after exiting the probe.

Microdialysis probes are by nature fragile and very small, which requires great care in inserting and withdrawing the probe from the tissue in which it is used. However, it is also of great importance that the probe when inserted into tissue of a living person, is placed in the intended location such that when measuring the probe actually through microdialysis measures the intended chemical/biological variables that at each measurement is of interest. It is of course important in these measurements to know exactly what is measured.

The use of microdialysis becoming more frequent and common raises other problems such as monitoring and control of the probe during insertion and use. It is a fact that microdialysis provides a unique possibility to examine the equilibrias of substances and/or the amounts present or missing of substances or to monitor specific changes in the status of substances connected with e.g. the use of medicaments, in surgery etc.

The monitoring and control of the probe position during insertion/withdrawal and use-has been an obstacle in so far that the smallness and the material of the probe does not make possible the use of common methods for detecting the probe once the insertion has been started. This becomes more problematic the deeper into the tissue the microdialysis is to take place.

SUMMARY OF THE INVENTION

It is thus an object of the invention is to provide a microdialysis probe, the location of which may be monitored and controlled using means such as X-rays or the like during insertion/withdrawal or during dialysis in order to facilitate the placement of the probe at a predetermined location and to control the location of the probe.

It is also an object of the invention to provide a microdialysis probe, which is suitable for the general use in living tissue when taking samples for e.g. diagnostic purposes.

In accordance with the invention, these and other objects evident from the description of the invention are accomplished in a microdialysis probe in that characterized by presence of a position indicating object imparting such characteristics to the distal part of the probe as to allow non-invasive examination of the location of the distal part of the microdialysis probe.

BRIEF DESCRIPTION OF THE DRAWINGS

The invention will now be described by way of example and with reference to the accompanying drawings in which:

FIG. 1 shows, partially in section, a first embodiment of a microdialysis probe in section according to the invention.

FIG. 2 shows a detailed view of the foremost part of the probe according to the embodiment as shown in FIG. 1.

DETAILED DESCRIPTION OF PREFERRED FORMS OF THE INVENTION

Figure 3A:
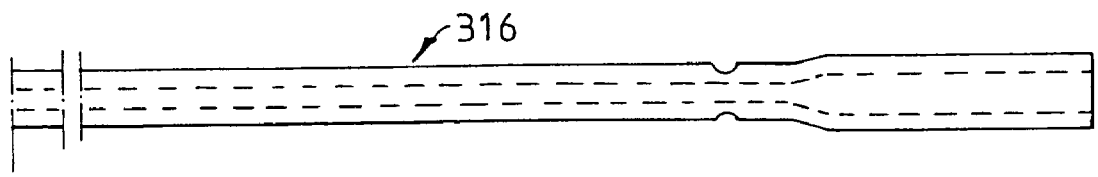
FIG. 3a–c shows in detail the sealing of the most distal part of the first tube according to the embodiment shown in FIG. 1 and FIG. 2.

A first embodiment of the microdialysis probe according to the invention is shown in FIG. 1 and FIG. 2. The probe exhibits a distal end piece 110 comprised of glue which holds and seals a plug 130 within the distal part of a membrane 115. This comprises the foremost tip of the probe. The membrane 115 is preferably tubular. A proximal tubular fitting 11 land a proximal end piece 113 comprises the other end of the probe as such. The proximal tubular fitting 111 is permanently fastened to a proximal end piece 113. The proximal end of the membrane 115 is fastened to the proximal tubular fitting 111.

In the proximal end piece 113 two tubes 107 and 108 constituting the inlet to the probe and the outlet from the probe are connected to the probe, such as to let the perfusion liquid pass through the same. Note in the definitions above the possibility of reversed flow.

Within the membrane 115, which is in the form of a tube made from semi-permeable material, and also within the proximal tubular fitting 111, a first tube 116 extends essentially from the proximal end of the probe to the distal end. The first tube 116 is closed at the most distal end by a position indicating object, a plug 130, and exhibits at least one aperture 117 at or near the distal end. The aperture 117 constitutes a passage for the perfusion liquid entering the space 118 defined by the first tube 116 and the dialysis membrane 115 in combination with the proximal tubular fitting 111 and the distal tubular fitting 112. For the withdrawal of the perfusion liquid a second tube 119 extends from the proximal end of the probe and opens up into the same space 118 somewhere near to the to the proximal end of the probe thereby forming an exit for the perfusion liquid. The perfusion liquid has now become a dialysate having acquired substances exchanged over the semi-permeable membrane. The distal end piece 110 of the probe may e.g. be fastened in a permanent way to the distal end of the first tube 116.

To give a proper understanding of the invention, exemplary dimensions are given here. The length of the probe may be e.g. 5 cm from the most distal end of the same to the proximal part of the proximal tubular fitting 111. The length of the tubular fitting may be approximately 2 cm, thus the length of the membrane may be approximately 3 cm. The diameter of the proximal tubular fitting may be approximately 1 mm and the outer diameter of the membrane may be approximately 0.6 mm.

The plug 130 shown in FIG. 2 may preferably be manufactured from gold. Other materials may of course be used but the reason for using gold is the ductility and the relative opaqueness for X-rays and also the chemical and physiological inertness exhibited by gold.

In a second embodiment the plug 130 may be made such as to make the distal end of the microdialysis probe visible during examination using NMR (Nuclear Magnetic Resonance).

This plug could e.g. have the form of a hollow amorphous plug filled with air or the like, which would impart characteristics to the plug such that it will be possible to locate the plug using NMR.

Figure 3B:
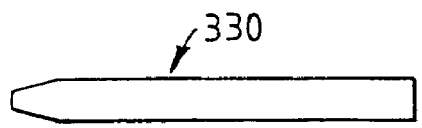
Figure 3C:
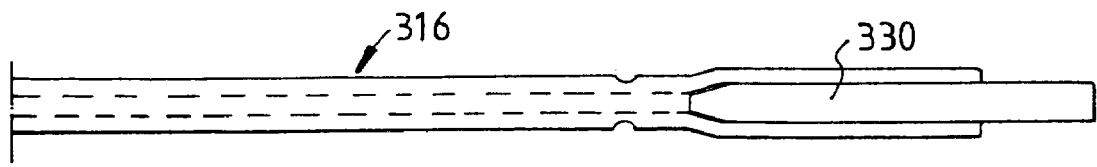

One way of accomplishing the sealing at the distal end of the first tube 316 is shown in FIG. 3a–c.

In FIG. 3a) the form of an exemplary first tube 316 according to the invention is shown. The tube has been subjected to corbelling in order to widen the diameter of the same enough to accommodate the sealing plug 330.

In FIG. 3b) a preferred embodiment of the sealing plug 330 is shown and in FIG. 3c) the first tube 316 with the sealing plug 330 in place is shown.

Figure 4:
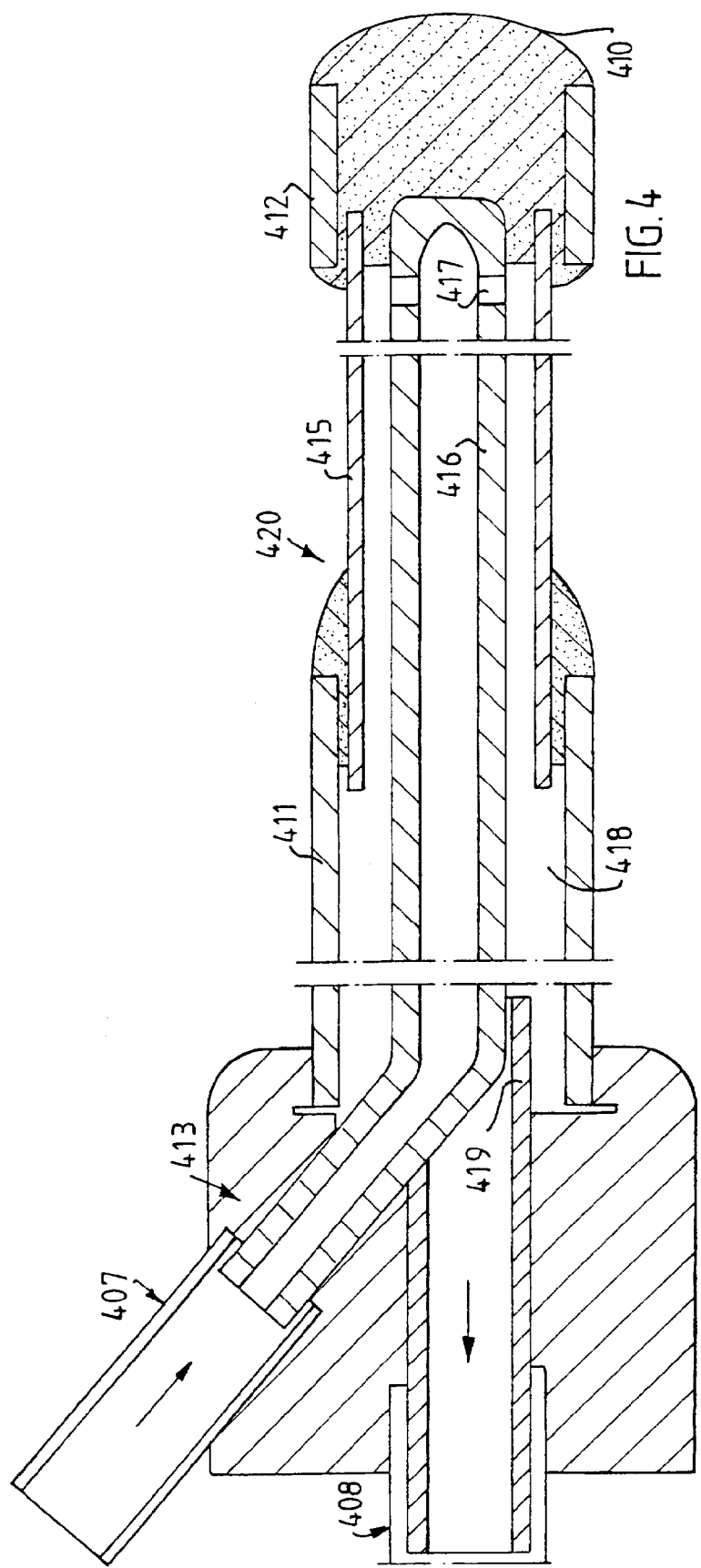
FIG. 4 shows a second embodiment of a microdialysis probe in section according to the invention.

A second embodiment of the microdialysis probe according to the invention is shown in FIG. 4. The probe exhibits a distal end piece 410 and a distal tubular fitting 412. The distal tubular fitting 412 in combination with the end piece 410 comprises the foremost tip of the probe. A proximal tubular fitting 411 and a proximal end piece 413 comprises the other end of the probe as such. The proximal tubular fitting 411 is permanently fastened to a proximal end piece 413. A membrane 415 is fastened to the distal tubular fitting 412, the membrane 415 having a smaller diameter than the fitting. The membrane is preferably tubular. The fitting 411 itself being closed at the most distal end thereof e.g. by using glue or the like, forming the distal end 410. The other end of the membrane 415 is fastened to the proximal tubular fitting 411. There is a tapered transition piece 420 between membrane 415 and fitting 411.

In order to accomplish an X-ray opaqueness of the foremost part of the probe the distal end may be formed as a half-sphere or the like from a material which is opaque to X-rays or the X-ray opaqueness creating material may be incorporated in the glue as such.

In the end proximal piece 413 two tubes 407 and 408 constituting the inlet to the probe and the outlet from the probe are connected to the probe, such as to let the perfusion liquid pass through the same. Note above the possibility of reversed flow.

In this embodiment the dimensions of the probe will be approximately the same as in the embodiment described in connection with FIG. 1.

Within the membrane 415, which is in the form of a tube made from semi-permeable material, first tube 416 extends essentially from the proximal end of the probe to the distal end. The first tube 416 has a closed distal end and has at least one aperture 417 at or near the distal end. The aperture 417 constitutes a passage for the perfusion liquid entering the space 418 defined by the first tube 416 and the dialysis membrane 415 in combination with the proximal tubular fitting 411 and the distal tubular fitting 412. For the withdrawal of the perfusion liquid a second tube 419 extends from the proximal end of the probe and opens up into the same space 418 somewhere near to the to the proximal end of the probe thereby forming an exit for the perfusion liquid.

In the same manner as has been described in connection with the first embodiment of the invention the end piece 410 sealing distal end of the probe may be made such as to make the same visible during examination using NMR (Nuclear Magnetic Resonance). This could e.g. be done by incorporating in the sealing glue a hollow amorphous plug filled with air or the like, which would impart characteristics to the distal end of the probe such that it will be possible to locate the probe end by using NMR.

The invention has been described under reference to embodiments of the same. It should be understood that the above describes an exemplary embodiment of the distal end of the probe itself and the constructive details thereof may vary within the scope of the claims or be independent of the constructive details of the distal end of the probe depending on different embodiments of the invention. The scope of the invention however is described by the appended claims.

What is claimed is:

1. A microdialysis probe, comprising:
   a first tube extending from a proximal end of the probe to a distal end of the probe;
   a membrane (115) mounted over an exterior surface of the first tube;
   a distal end piece (110) comprising
   a distal end portion of the first tube (116);
   a distal end portion of the membrane (115) mounted over an exterior surface of the first tube;
   a position indicating object (130) inserted into the distal end of the first tube; and
   a space (118) defined by and located between an exterior of the first tube and an interior surface of the membrane;
   a proximal tubular fitting (111) attached to the distal end piece (110);
   a proximal end of the membrane being fastened to the proximal tubular fitting (111);
   a proximal end piece (113) permanently fastened to the proximal tubular fitting;
   two further tubes (107, 108) located in the proximal end piece and forming an inlet and an outlet from the probe to let a perfusion liquid pass through the probe;
   an aperture (117) through a wall portion of the first tube and located adjacent the distal end of the first tube and providing a perfusion liquid communication passage between the space (118) and the interior of the first tube; wherein,
   the position indicating object allows non-invasive location of the distal part of the probe when inserted in patient tissue.

2. The probe of claim 1, wherein the position indicating object is a plug comprising a glue that seals in the distal end of the first tube and the distal end part of the membrane.

3. The probe of claim 1, wherein the membrane is tubular and semi-permeable material.

4. The probe of claim 1, wherein the distal end piece is permanently fastened to the distal end of the first tube.

5. The probe of claim 1, wherein,
   a length of the probe is 5 cm,
   a length of the proximal tubular fitting is 2 cm,
   a length of the membrane is 3 cm,
   a diameter of the proximal tubular fitting is 1 mm, and
   an outer diameter of the membrane is 0.6 mm, the dimension being approximate.

6. The probe of claim 1, wherein the position indicating object is a plug of gold.

7. The probe of claim 1, wherein the position indicating object is visible to X-rays.

8. The probe of claim 1, wherein the position indicating object permits the distal end of the probe to be visible, during examination, using Nuclear Magnetic Resonance.

9. The probe of claim 1, wherein the position indicating object is a hollow plug filled with air, the plug being identifiable using Nuclear Magnetic Resonance.

10. The probe of claim 1, wherein,
the distal end portion of the first tube (116) has a end with a widened interior diameter as compared to an interior diameter of a proximal end of the first tube, and
the position indicating object sealingly extends into the end.

11. A microdialysis probe, comprising:
an interior first tube extending from a proximal end of the probe to a distal end of the probe, the first tube being closed at the distal end of the probe;
a membrane;
a distal end piece comprising
a distal end portion of the first tube;
a position indicating object;
a first portion of the membrane coextensive with the first tube and extending beyond the distal end of the first tube; and
a space located between an exterior of the first tube and an interior surface of the membrane;
a proximal tubular fitting attached to the distal end piece;
a proximal end of the membrane being fastened to the proximal tubular fitting;
a proximal end piece fastened to the proximal tubular fitting;
two further tubes located in the proximal end piece and forming an inlet and an outlet from the probe to let a perfusion liquid pass through the probe;
an aperture located adjacent the distal end of the first tube and providing a perfusion liquid communication passage between the space and the interior of the first tube; wherein,
the position indicating object allows non-invasive location of the distal part of the probe when inserted in patient tissue.

12. The microdialysis probe of claim 11,
the distal end piece (410) further comprising a distal tubular fitting (412) forming a foremost tip of a distal end of the probe;
the proximal end piece (413) forming the proximal end of the probe;
the proximal tubular fitting (411) attached to the proximal end piece at the proximal end;
the membrane (415) fit, at a first end, to the proximal tubular fitting (411), and fastened, at a second end, to the distal end piece (410);
the first tube (416) extending, through the proximal tubular fitting, from the proximal end piece (413) to the distal end piece (410), the first tube being closed at a distal end;
a second tube (419) extending from the proximal end of the probe to the space;
the aperture (417) is located through a wall portion of the first tube and is located adjacent the distal end of the first tube providing a perfusion liquid communication passage between the space (418) and the interior of the first tube; wherein,
the distal end piece (410) is the position indicating object allowing non-invasive location of the distal part of the probe when inserted in patient tissue.

13. The probe of claim 12, wherein the position indicating object is a plug comprising a glue that seals in the distal end of the first tube and the distal end part of the membrane.

14. The probe of claim 13, wherein the distal end piece comprises a plug of gold.

15. The probe of claim 12, wherein distal end piece is a rounded shape of a material opaque to X-rays.

16. The probe of claim 12, wherein the membrane is tubular and semi-permeable material.

17. The probe of claim 12, wherein the distal end piece is permanently fastened to the distal end of the first tube.

18. The probe of claim 12, wherein the position indicating object is visible to X-rays.

19. The probe of claim 12, wherein the position indicating object permits the distal end of the probe to be visible, during examination, using Nuclear Magnetic Resonance.

20. The probe of claim 12, wherein the position indicating object is a hollow plug filled with air, the plug being identifiable using Nuclear Magnetic Resonance.

* * * * *